United States Patent [19]
Warden et al.

[11] 4,266,933
[45] May 12, 1981

[54] ROTARY DENTAL POLISHING APPARATUS

[76] Inventors: Fuller Warden, 1231 E. 30th Pl., Tulsa, Okla. 74114; Eugene W. Lewis, 5415 S. 68 E. Pl., Tulsa, Okla. 74145

[21] Appl. No.: 61,764

[22] Filed: Jul. 30, 1979

[51] Int. Cl.³ .............................................. A61C 1/12
[52] U.S. Cl. .................................... 433/82; 433/125; 222/161
[58] Field of Search ........................ 433/82, 83, 84, 85, 433/87, 81, 89, 125, 166; 15/31; 222/167, 168

[56] References Cited

U.S. PATENT DOCUMENTS

| | | | |
|---|---|---|---|
| 2,300,828 | 11/1942 | Goldenberg | 433/166 |
| 3,389,468 | 6/1968 | Lewis et al. | 433/82 |
| 3,472,045 | 10/1969 | Nelsen et al. | 433/125 |
| 3,509,630 | 5/1970 | Spinello | 433/82 |
| 3,579,835 | 5/1971 | Levenson | 433/82 |
| 3,715,806 | 2/1973 | Warden et al. | 433/83 |

*Primary Examiner*—Gene Mancene
*Assistant Examiner*—John J. Wilson
*Attorney, Agent, or Firm*—James H. Chafin

[57] ABSTRACT

A rotary dental polishing apparatus which utilizes a rotatably cylindrical cartridge for containing polishing paste therein. One end of the cartridge is provided with a polishing cup, the cavity of which is in communication with the interior of the cartridge to receive paste therefrom. The cartridge also comprises a wiper conveyer mechanism which is in communication with the outer end of the cartridge at the end opposite the cup and is prevented from rotating which results in the conveyer mechanism continuously urging the paste out of the cartridge into the cup. The cartridge may be configured to rotate at a right angle to the drive source.

18 Claims, 18 Drawing Figures

ROTARY DENTAL POLISHING APPARATUS

BACKGROUND OF THE INVENTION

1. Field of the Invention

The present invention relates to dental polishing apparatus for use in the dentist's office or for home personal use and more particularly, but not by way of limitation, to a rotary dental cleaning and polishing apparatus which carries its own supply of polishing compound and which automatically and continuously feeds said compound into a rotary polishing cup during the cleaning and polishing operation.

2. History of the Prior Art

People have been trying to keep their teeth clean for many years in order to prevent and control dental disease, maintain a healthy and pleasing appearance in an effort to retain their natural teeth for a lifetime. People have sought professional dental services and they have used various means, aids, regimes, materials and the like at home in an effort to keep their mouths clean and free of the causes of dental disease.

Until recent years, the cause of dental disease, namely dental caries and periodontal disease, was not generally well understood. However, in the past 20 years laboratory and clinical research in the field of preventive denistry have provided the dental profession with the knowledge of the cause of such disease. The principal cause and initiating factor in the production of caries and periodontal disease is the formation and accumulation of an adherent bacterial colonization on tooth surfaces known as dental plaque.

Dental plaque is an adherent mass that cannot be removed by liquid agitation, but must be mechanically removed. When the plaque is allowed to remain on the tooth surface, undisturbed, for a period of more than 24 hours and is given a food supply of refined carbohydrates, nutrient secretions from the oral soft tissues and the like, it assimilates and digests these food supplies, producing toxic chemical waste products that in turn initiate the damaging break down of the teeth and supporting gum and bone tissue. An acid waste product is produced and held on the tooth surface which dissolves tooth enamel resulting in a caries or decay lesion which the body is not capable of repairing.

A noxious waste product is produced and absorbed by the supporting gum tissue resulting in an inflamatory reaction which the body is capable of reversing if the dental plaque is removed on a regular basis. However, if the plaque is not removed on a regular basis, it can become mineralized and form a hard plaque known as calculus or tartar that cannot be removed without the scaling procedure of a professional oral prophylaxis.

Thus, a thorough professional tooth cleaning which does remove plaque, stain and debris from the teeth is only totally effective in controlling dental disease for approximately 24 hours and therefore has no sustained effect on dental disease prevention.

In the past, the dental profession has educated the public to brush and clean the teeth at least twice a day to prevent and control dental disease, and more recently, preventive dentists have promulgated and taught a plaque control program of regular personal oral hygiene. Various aids and devices along with the conventional toothbrush have been recommended and used to keep plaque, stains and debris off the teeth between dental office visits such as by the use of dental floss.

Current statistics indicate that dental disease is not being significantly prevented or controlled despite regular professional cleanings and good home personal oral hygiene. People are constantly advised to use flouride toothpastes, rinses or gels and the like to fortify teeth against decay acids or to aid in reducing sensitivity. The problem here is that one cannot get the flouride ions to the enamel of the tooth that is covered with plaque.

Attempts have been made to provide tooth cleaning and polishing devices which if properly used could be somewhat effective in the removal of plaque. One such device is simply a rotatable polishing cup located at the outer end of a motor drive shaft whereby one may apply cleaning and polishing paste to the cup and then polish the front surface of the teeth.

However, such devices while being adequate to clean and polish the front surface of the teeth, do not allow complete cleaning of the other parts of the teeth. Such devices further require a great amount of dexterity in the filling of the cup with paste and the handling of the filled cup properly when it is carried to the teeth.

The dentist, on the other hand, in cleaning teeth at the office utilizes a prophy angle in which a cup is set at right angles to the drive shaft of the rotary hand piece which allows the dentist to effectively clean and polish the total exposed surfaces of the teeth.

However, the dentist or oral hygienist must repeatedly stop and fill the cup with polishing paste which is time-consumming and results in uneven polishing due to the varying amounts of paste in the cup throughout the cleaning operation.

Attempts have been made to provide the dentist or oral hygienist with a prophy angle wherein a continuous flow of paste is provided to the cup from within the hand piece. Two such devices are taught in the patents to Fritz Deuschale, U.S. Pat. No. 3,691,636, issued Sept. 6, 1972 for a "Dental Prophylactic Device" and the patent to E. W. Lewis et al, U.S. Pat. No. 3,389,468, issued June 25, 1968, for a "Disposable Pre-Charged Dental Hand Piece".

However, such devices require a rather complicated gearing mechanism which permits a drive shaft member to extend through the paste carrying cartridge and not only serve as a means to push the polishing compound out of the cartridge but also to rotatingly drive the polishing cup through right angle gearing.

For these reasons, no one has been able to successfully get such devices to the market to fill this long-felt need.

SUMMARY OF THE INVENTION

The present invention contemplates a tooth polishing device which couples a disposable pre-charged cartridge and polishing cup with a rotary power source for use in the dental office as well as for general public home use. The device is designed and constructed to overcome the disadvantages of the prior art and could replace the use of prophy angles in the dentist's office. The present invention will provide the general public with a device that can positively and effectively remove dental plaque, stain and debris with each use in the same manner that is accomplished in the dental office periodically.

It is a most worthwhile object of the present invention to accomplish what preventive dentists have been trying to effect in their patients for 20 years; a device and method that the patient can use for regular home care which is effective enough to remove dental plaque and thus prevent and control the principal dental maladies of dental caries and periodontal disease.

It is a further object of the invention to provide a home polishing device that is a more effective remover of plaque, stain and debris than the conventional hand toothbrush, automatic toothbrushes and polishers, toothpaste and all other aids presently used.

It is a further object of the present invention to provide pre-filled cartridge with different kinds of polishing paste for maintenance and plaque removal, stain removal, desentization, flouride preventive, subgingival curettage, artificial dentures and plaque disclosing.

The present invention provides a disposable cylindrical cartridge body for carrying the cleaning and polishing compound which is usually in the form of a paste. The cartridge may be pre-filled with different types of compound for various uses such as plaque removal, subgingival curettage, or agents for polishing tooth restroations.

A polishing cup is attached to one end of the cartridge, the cavity of said cup being in communication with the interior of the cartridge by way of a simple orifice.

The cartridge body is provided with means for connection to a motor drive shaft such that the entire cartridge body and associated polishing cup will be made to rotate together. This eliminates complicated and costly combination drive shafts and conveyers which are coupled with passageways for moving the paste out of the cartridge and into the polishing cup.

A spiral wiper element is disposed in the cartridge in order to move the paste toward the polishing cup. The end of the wiper element is operably connected to the hand piece fixed housing in order to prevent its rotation within the cartridge. Therefore, it does not have to act as both conveyer and drive shaft for the polishing cup as is true with the prior art.

The cartridge may be configured to be parallel with the drive shaft to provide a device for polishing the front surface of teeth or may be packaged in a shorter configuration and driven at a right angle to the drive shaft to replace the dental prophy angle. Further, the device may be driven by its own power source, AC or DC, or by the dentist's rotary hand piece (doriot).

DESCRIPTION OF THE DRAWINGS

Other and further objects and advantageous features of the present invention will hereinafter more fully appear in connection with a detailed description of the drawings in which.

DESCRIPTION OF THE PREFERRED EMBODIMENTS

Figures 1, 2, 3:
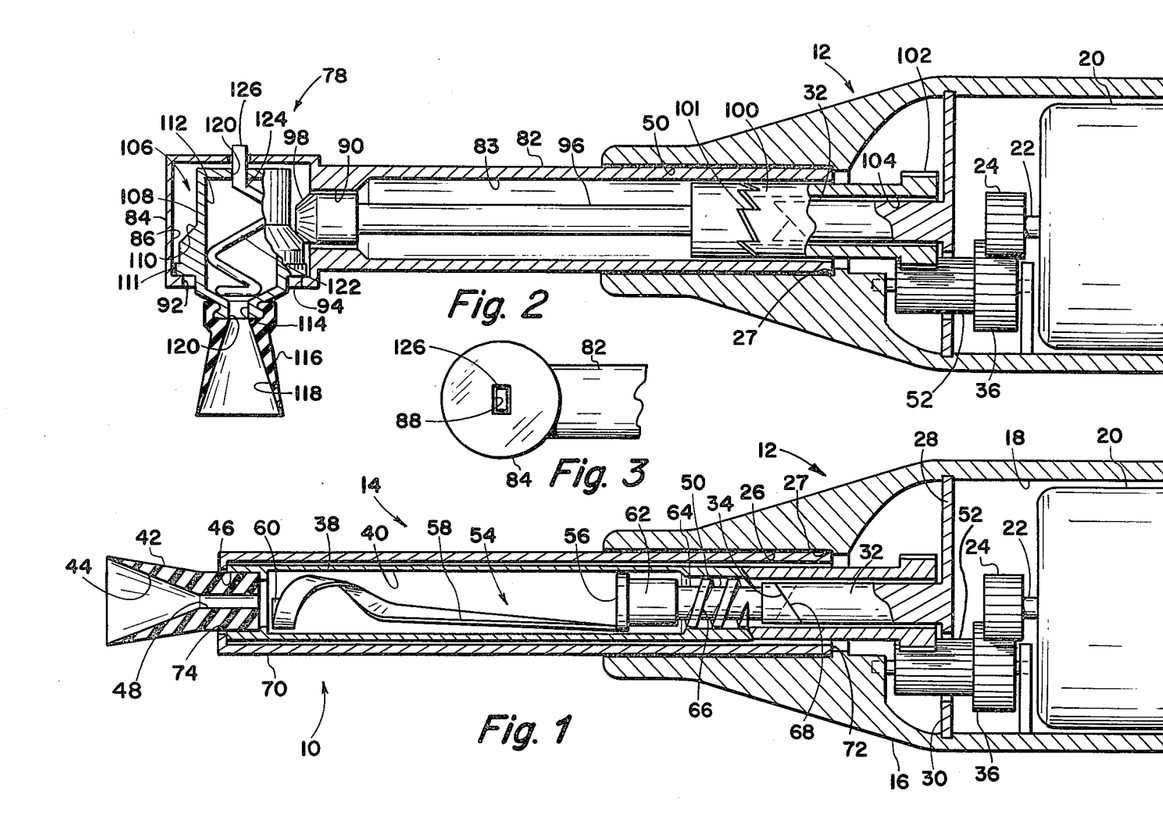
FIG. 1 is a sectional view of a dental polishing apparatus embodying the present invention.
FIG. 2 is an elevational sectional view of a second embodiment of the invention.
FIG. 3 is a partial plan view of the apparatus of FIG. 2.

Referring to the drawings in detail, reference character 10 generally indicates a rotary dental polishing apparatus which comprises a drive mechanism generally indicated by reference character 12 and a polishing device generally indicated by reference character 14.

The drive mechanism 12 comprises a housing 16 having an internal cavity portion 18 which houses a drive motor 20. The drive motor may be of an electrical AC motor or a DC motor. The motor 20 has an output shaft 22 which is provided with a suitable gear member 24.

One end of the housing is provided with a cylindrical passageway 26 which is in communication with the cavity 18 and terminates adjacent the forward end of the cavity 18 in an annular stop shoulder 27.

Also provided in the cavity 18 is a partition member 28 which is rigidly secured to the inside of the housing. The partition member 28 is provided with an off-center aperture 30 for a purpose that will be hereinafter set forth. The partition member 28 is also provided with a forwardly extending stud member 32, the outer end of which is provided with a wrenching element 34 which may take on any one of several configurations, the one shown being hereinafter more fully described.

A second two-stage gear member 36 is journalled within the cavity 18, one portion of the gear 36 being in meshing engagement with the drive shaft gear member 24. The second stage of the gear member 36 extends forwardly through the port 30 and the partition member 28.

The tooth polishing device 14 generally consists of a disposable cartridge comprising a cylindrical cartridge body member 38 which is hollow thereby providing an interior cylindrical cavity portion 40. A rotary polishing cup 42 which is made of elastic or rubber compound material usually having a truncated conical shaped cavity portion 44 is rigidly attached to the outer end of the cartridge body 38 by either adhesive or frictional contact at the surface 46.

The cup 42 is provided with an internal longitudinal passageway 48 which provides an orifice for open communication between the cavity 44 of the cup and the interior cavity 40 of the cartridge body.

The opposite end of the cartridge body 38 is provided with a longitudinal cylindrical passageway 50. The outer periphery of the end portion of the cartridge body 38 is provided with a gear member 52 which may be made as an integral part of the cartridge body. The gear teeth of the gear 52 are capable of meshing engagement with the gear member 36 as shown. The elongated longitudinal passageway 50 is of a size to permit receiving the stud member 32 therein.

A wiper conveyer mechanism generally indicated by reference character 54 is disposed within the cavity 40 of the cartridge body 38 and is for the purpose of urging the paste carried by said cavity toward the end of the cartridge carrying the cup member 42. The wiper conveyer mechanism generally comprises a disc member 56 which is slidably disposed within the cavity 40.

The forward end of the disc member 56 is provided with a helical ribbon flight conveyer member 58 which has a helical spiral configuration and terminates at a forward end in an acute helical spiral at about reference character 60.

Stated another way, the ribbon flight member 58 is attached to the outer periphery of the forward surface of the disc member 56 and forms a gentle helical curve near the inside surface of the cartridge body 38 which will serve to wipe the paste material from the inside walls of the cavity 40 and gently urge the paste material toward the forward end of the cavity. As the ribbon flight member 58 approaches its outer end, the spiral becomes tighter which serves to apply more pressure to the paste in order to urge the paste through the orifice 48 of the cup member 42.

This ribbon flight 58 may take on the form of a flat spiral ribbon flight or success has even been obtained with configuring said ribbon flight member from a simple piece of cylindrical wire material. It should be pointed out that in this application, the barrel of the cartridge rotates instead of the conveyer.

A cylindrical plug member 62 is secured to the interface of the disc member 56 and extends rearwardly therefrom for a short distance. The inner end of the plug member 62 is provided with an inwardly extending shaft 64 which is provided with a screw type conveyer element 66 around the outer periphery thereof. Both the plug member 62 and the outer periphery of the screw conveyer element 66 have an outside diameter approximately equal to the inside diameter of the longitudinal passageway 50.

The inner end of the shaft 64 is provided with a wrenching element 68 which is meshingly engagable with the wrenching element 34 of the housing stud member 32. The wrenching elements 34 and 68 are constructed identically to lock the shaft 64 against rotation with respect to the stud member 32.

A housing adapter which constitutes an elongated cylindrical sleeve member 70 is opened at the inner end 72 thereof, the outer end being provided with a reduced aperture 74. The outer diameter of the housing adapter 70 is sized to snugly fit the inner diameter of the housing passageway 26 so that when the housing adapter 70 is pushed within the passageway 26 it may be tight fitting and pushed inwardly until the end 72 thereof is stopped by the annular shoulder 27 of the housing.

Figures 4, 5, 6, 8, 10:
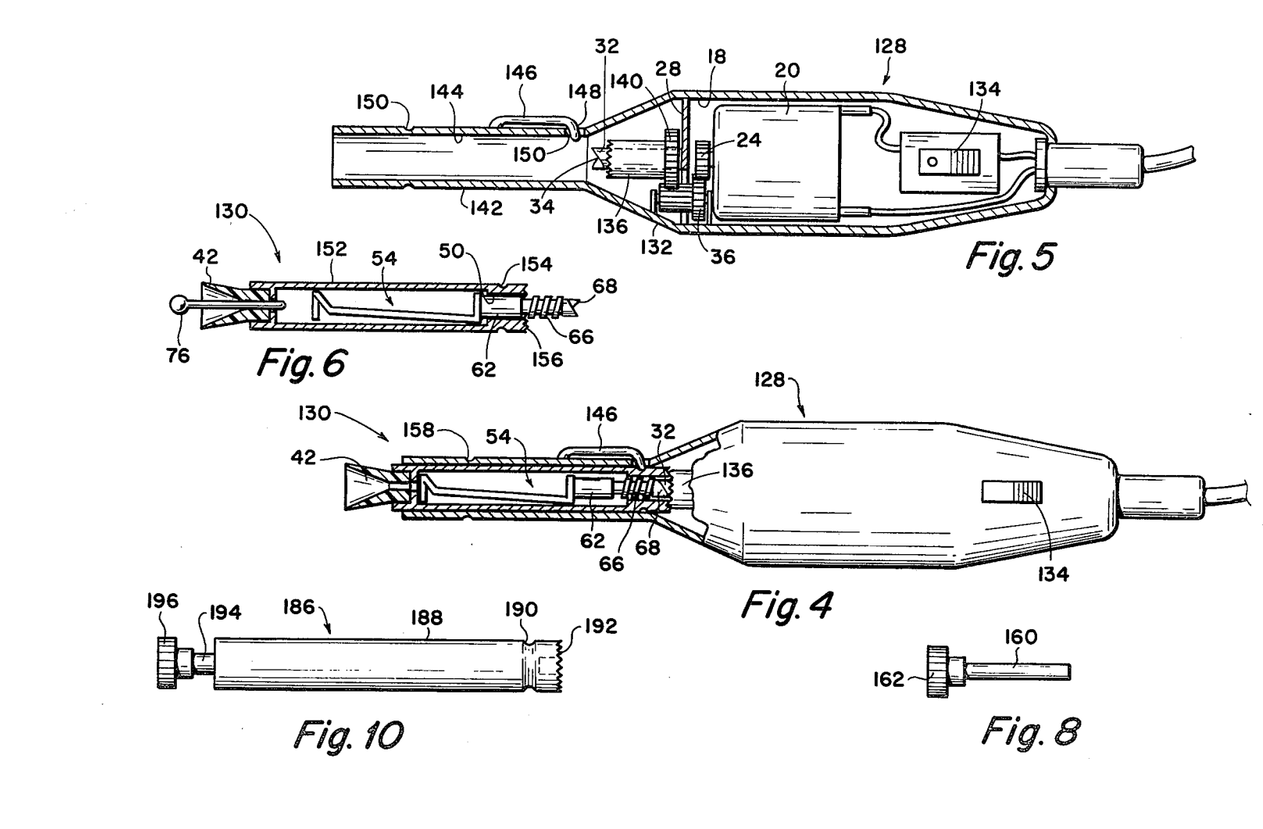
FIG. 4 is a view, partially in section, of a modification of the embodiment of FIG. 1.
FIG. 5 is a detailed sectional view of the drive mechanism of the apparatus of FIG. 4.
FIG. 6 is a detailed sectional view of the polishing device of the apparatus of FIG. 4.
FIG. 8 is a detail of the drive adapter of the apparatus of FIG. 7.
FIG. 10 is a detail of the drive adapter of the apparatus of FIG. 9.

In use, the cartridge housing 38 with cup member 42 attached to one end thereof is pre-filled with dental polishing, treating or cleaning compound. The outer end of the cartridge member may be provided with a removable plugging member 76 as shown in FIG. 6. The wiper conveyer mechanism 54 is in a retracted position so that the plug member 62 is sealingly engaged with the longitudinal passageway 50, again which is clearly shown in FIG. 6 of the drawings and which serves, in conjunction with the plug member 76 to close off the interior of the cartridge containing the paste material.

Referring back to FIG. 1, the cartridge is inserted within the housing adapter 70 so that the flexible cup member 42 protrudes out of the outer end of the housing adater 70. The housing adapter with associated cartridge is then inserted within the passageway 26 of the drive mechanism 12. As the housing adapter 70 and associated cartridge 38 is being inserted within the passageway 26, the wrenching element 68 of the cartridge assembly comes into meshing engagement with the wrenching element 34 of the housing assembly.

As the housing adapter then is fully pushed into the passageway 26 until the end 72 thereof comes in contact with the annular stop shoulder 27, the housing stud member 32 will force the wiper conveyer mechanism 54 forwardly within the cavity 38 and into the position as shown in FIG. 1. This sliding movement of the wiper conveyer mechanism 54 accomplishes two purposes, the first being for the disc member 56 to push a certain amount of the paste forward so it starts coming out of the cup 42 immediately, and secondly to unplug the plug member 62 from the longitudinal passageway 50. The screw type conveyer element 66 is arranged on the shaft member 64 and serves to prevent paste that might have gotten past the disc member 56 from traveling along the shaft 64 toward the interior of the housing.

As the motor 20 is put into operation, the drive shaft gear member 24 imparts rotation to the two-stage gear 36 which in turn causes the entire cylindrical cartridge member 38 and attached polishing cup 42 to rotate. The cooperating wrenching elements 68 and 34 serve to prevent rotation of the wiper conveyer mechanism 54 so that the cartridge housing 38 and paste therein is being rotated with respect to the ribbon flight element 58 in order to force the paste compound material forwardly through the orifice 48 into the cavity 44 of the cup member 42. Natrually if more positive drive of the paste material from the cartridge 38 is desired, the ribbon flight conveyer member 58 may be re-configured to a tighter spiral or may even be replaced by a screw type conveyer element.

Referring now to FIGS. 2 and 3, reference character 78 generally indicates a second embodiment of the polishing device which may be utilized with the drive housing mechanism 12 hereinbefore described in conjunction with the apparatus of FIG. 1. In this case the drive device comprises a housing adapter 80 which consists of an elongated sleeve member 82 having outside diameter substantially equal to the inside diameter of the longitudinal housing passageway 50 so that the open end of the sleeve member 82 may be inserted within said passageway 50 against the annular stop member 27. The sleeve member 82 is hollow providing a longitudinal cavity portion 83 therein.

The outer end of the sleeve member 82 is provided with a second cylindrical housing portion 84, the longitudinal axis of which is set at a right angle to the longitudinal axis of the sleeve member 82. The housing portion 84 is provided with an internal cylindrical cavity 86, the upper portion of which is closed and provided with a rectangular aperture 88 in the central portion thereof. The juncture between the housing member 84 and the sleeve member 82 is provided with a longitudinal passageway 90 which provides communication between the cavity 86 and the sleeve member cavity 83.

The lower end of the housing portion 84 is provided with an enlarged aperture 92 therethrough having an inwardly extending flange or lip 94. An elongated drive shaft extension member 96 is journalled within the sleeve member 82, the outer end thereof being provided with a bevel gear member 98 which extends through the passageway 90 into the cavity 86 of the housing portion 84.

The opposite end of the shaft 96 is provided with an enlarged shaft segment 100 the end of which is provided with a plurality of gear teeth 102 around the outer periphery thereof the gear teeth 102 being capable of meshing engagement with the two-stage gear member 36. The shaft segment 100 is provided with a hollow cavity 104 for receiving the housing stud member 32 therein. It is noted in this application that the stud member 32 has no operational function. It is also noted that the shaft segment 100 may be broken at 101 and provided with opposing gear members so that the inner end having the gear 102 is rotatably carried by the housing.

A cartridge assembly generally indicated by reference character 106 is insertable into the cavity 86 of the housing section 84 for rotation therein. The cartridge assembly 106 generally comprises a cylindrical cartridge body 108, the lower end of which is provided with a bevel gear 110 around the periphery thereof which is meshably engagable with the bevel gear 98 of the drive shaft 96. A flange member 111 is provided around the base of the bevel gear 98. The interior of the cartridge body 108 is hollow providing a cylindrical cavity 112 for holding a paste compound therein. The lower end of the cartridge body 108 is provided with an aperture 114. The opposite end of the cartridge body 108 is provided with an opening 120 therein.

A helical conveyer member 122 is journalled within the cavity 112 of the cartridge body 108, the upper end thereof being provided with a shaft member 124 which is journalled within the aperture 120 of the cartridge body 108. A rectangular shaped wrenching element 126 is secured to the upper end of the shaft 124 and is extendable upwardly through the rectangular aperture 88 in the top of the housing section 84 as shown in FIGS. 2 and 3. The shape of the rectangular protrusion 126 and the rectangular aperture 88 of the housing are such that when the cartridge body 108 is rotated within the housing portion 84, the protrusion 126, its associated shaft 124 and the ribbon flight conveyor member 122 are prevented from rotating.

In use, the cartridge assembly 106 is pre-loaded with a polishing, cleaning or treating paste compound and may be sealed with a suitable plug member 76 as shown in FIG. 6. The cartridge then may be inserted through the opening 92 in the housing portion 84 until the flange member 111 passes the inwardly extending lip member 94 thereby locking the cartridge body 108 within the housing portion 84 such that the beveled gears 110 and 98 are in meshing engagement.

When the cartridge body 108 is fully inserted within the housing portion 84, the protrusion 126 will be engaged with the rectangular aperture 88 of the housing to prevent rotation of the helical conveyor 122 as hereinbefore set forth.

When the motor 20 is made to operate, the rotational power thereof is transmitted through the gear member 24 to the two-stage gear 36 wherein the rotational power is transferred by means of the gear 102 to cause the shaft 96 to rotate. Rotation of the cartridge housing 108 then is effected by the cooperating beveled gear members 98 and 110. Rotation of the cartridge housing 108 cooperating with the stationary ribbon flight conveyor 122 therein will cause the paste to be pushed toward the cup member 116 and dispensed within the cavity 118 thereof for polishing the teeth.

It can readily be seen at this point that the configuration described in relation to the drawing of FIG. 1 permits the polishing of the front surfaces of the teeth by the rotation of the cup member 42 and the continuous dispensing of polishing compound thereto. The device described in relation to FIGS. 2 and 3 relates to a rotatable cartridge device that works on the same principle as the device of FIG. 1 but is disposed at a right angle with respect to the drive shaft mechanism so that the device may be used as a prophy angle either by the dentist or by home use to clean the front back and biting surfaces of the teeth for a more complete dental cleaning polishing operation.

Referring now to FIG. 4 reference character 128 generally indicates a drive housing assembly for use in conjunction with a disposable cartridge polishing device generally indicated by reference character 130. FIG. 4 depicts the two elements 128 and 130 assembled and ready for use while FIG. 5 depicts a detail of the housing assembly 128 and FIG. 6 depicts a detail of the cartridge assembly 130. Since the housing assembly 128 is similar to the drive housing 12 described in relation to FIGS. 1, 2 and 3, the common elements thereof will be described with common reference characters.

The drive housing 128 generally comprises a housing body 132 having a cavity portion 18 therein for supporting the motor 20, associated drive gear 24 and two-stage gear member 36. The housing is also provided with the partition member 28 having an aperture for receiving the forward end portion of the two-stage gear 36 therethrough. The partition 28 is also provided with the forwardly extending stud member 32 having the wrenching element 34 at the outer end thereof. The motor 20 is connectable by suitable wiring to either an AC or DC power source (not shown) through a switch member 134 which is accessible outside the housing.

An elongated sleeve member 136 is journalled on the outside of the shaft or stud member 32 and is provided with a plurality of gear teeth or serrations 138 around the forward end thereof. The rear end of the sleeve member 136 is provided with a plurality of gear teeth 140 around the outer periphery thereof, said gear teeth 140 being in meshing engagement with the gear teeth of the two-stage gear member 36.

The housing body 132 is also provided with a forwardly extending elongated housing extension 142 which is open at the outer end and has a cylindrical passageway 144 therethrough. A yieldable keeper member 146 is secured to the outer periphery of the extension member 144, the inner end of said keeper member 146 having a downwardly extending finger member 148. The housing 144 is also provided with an aperture 150 therein for receiving the finger member 148 therethrough.

The cartridge assembly 130 is substantially identical to the cartridge assembly of the polishing device 14 of the apparatus of FIG. 1. However, the cartridge assembly 130 has a cylindrical cartridge body 152 which is provided with an annular groove 154 near the inner end thereof for receiving the finger member 148 of the keeper member 146 as shown in FIG. 4. The inner end of the cartridge body 152 is provided with a plurality of gear teeth or serrations 156 which are meshably engageable with the gear teeth serrations 138 of the sleeve member 136.

Again, in use the cartridge assembly 130 is preloaded with a polishing paste material and the aperture in the cup is provided with a suitable removable plug member 76. The wiper conveyor assembly 54 is positioned inwardly within the cartridge body 152 so that the plugging cylinder 62 is engaged within the longitudinal cylindrical passageway 50.

When the cartridge assembly 130 is inserted into the housing extension 142, the wrenching element 68 of the conveyor wiper assembly 54 engages the wrenching element 34 of the stud member 32. As the cartridge body 152 is fully inserted into the housing extension 142, the keeper finger member 148 snaps into engagement with the annular groove 154 to hold the cartridge assembly 130 longitudinally in place within the drive assembly 128. This also serves to push the conveyor wiper mechanism 54 forwardly within the cartridge which again pushes some of the paste toward the cup member 42 and brings the screw conveyor element 66 into contact with the longitudinal passageway 50. The operation of the device of FIG. 4 then is identical with the operation of the device of FIG. 1. When the motor 20 is engaged, rotation is transferred to the cartridge housing 152 by means of the rotatable sleeve member 136 and the drive gears 24 and 36.

It is also noted at this point that the outer periphery of the housing extension 142 is provided with an annular groove 158 therearound for a purpose that will be hereinafter set forth.

Figure 7:
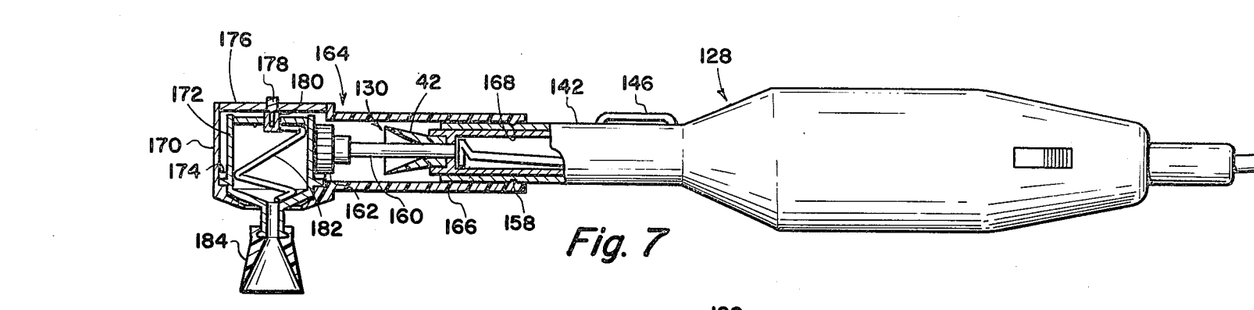
FIG. 7 is an elevational view, partially in section, of a modification of the apparatus of FIG. 2.

Referring to FIGS. 7 and 8 the drive housing assembly 128 and associated cartridge assembly 130 may be utilized to convert the polishing apparatus to a right angle polishing device. This is accomplished by means of a drive adapter shaft 160 having a gear member 162 on the outer end thereof. This drive adapter is shown in detail in FIG. 8 and shown in an assembled form in FIG. 7.

A right angle housing adapter generally indicated by reference character 164 is provided to complete the right angle assembly. The right angle housing adapter 164 generally comprises a cylindrical sleeve member 166 having an inwardly extending annular ridge member 168 around the inner periphery thereof which are engagable with the annular groove 158 of the drive housing assembly 128. The sleeve member 166 would of necessity be manufactured of a yieldable material so that it may be slidably disposed over the housing extension 142 until the cooperating ridge 168 and groove 158 come into contact.

The right angle drive housing 164 is constructed similar to the right angle drive housing described in relation to FIGS. 2 and 3 in that it further comprises a right angle cylindrical housing section 170 for journably receiving a cartridge body 172 therein. The cartridge body 172 is substantially identical to the cartridge body 108 described in FIG. 2. However, in this case instead of utilizing a beveled gear around the outer periphery thereof, an annular gear member 174 is secured to the outer periphery of the housing 172 for meshing engagement with the drive adapter gear 162. Also, the housing portion 170 may be provided with a top plate member 176 having a suitable wrenching element which is engagable with a wrenching element 180 of a wiper conveyor element 182 disposed within the cartridge body 172. Again a polishing cup member 184 is secured to the lower end of the cartridge housing for simultaneous rotation therewith.

Therefore, the right angle polishing device of FIG. 7 may be made as a disposable cartridge including both the cartridge body 172 and the housing adapter 164. Stated another way, the entire device may be made as a single unit whereby the cartridge is pre-filled and is inserted into the housing portion 170. The top plate member 176 is then secured to the top of the housing portion 170 to complete the disposable unit.

In use an expended cartridge assembly 130 may be left in the housing assembly 128. The drive adapter shaft 160 then is forced through the aperture within the cup member 42 so that the drive shaft will rotate with said cup member.

The housing adapter 164 with the charged cartridge body 172 therein is pushed over the drive adapter 160 and over the housing extension 142 until the inwardly extending ridge 168 snaps into engagement within the groove 158. The device is then ready to operate in a manner similar to that hereinbefore described. However, in this case rotation is imparted to the cartridge body 172 by means of the expended cartridge assembly 130 and drive adapter shaft 160.

Figures 9, 11:
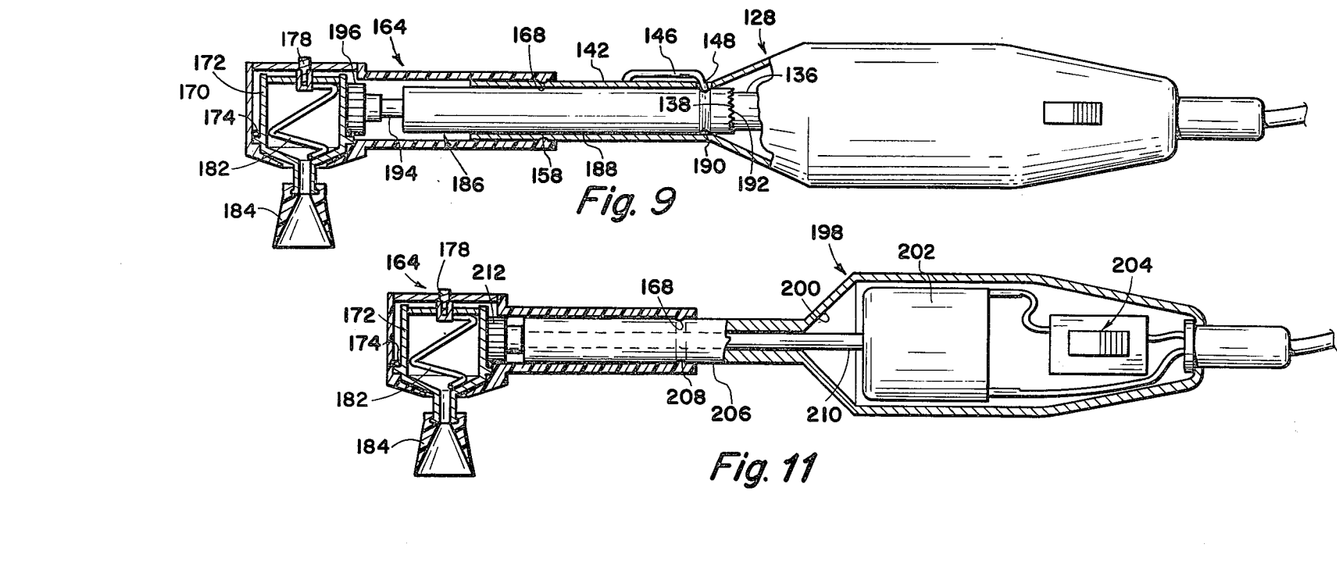
FIG. 9 is an elevational view, partially in section, of a second modification of the apparatus of FIG. 2.
FIG. 11 is an elevational view, partially in section of a third modification of the apparatus of FIG. 2.

Referring now to FIGS. 9 and 10, a second embodiment of the drive adapter generally indicated by reference character 186 may be used in place of the drive adapter 160 hereinbefore described. The drive adapter 186 generally comprises an elongated sleeve member 188 having an annular groove 190 near the inner end thereof, the inner end being provided with a plurality of gear teeth members or serrations 192. The outer end of the shaft member 188 is provided with a smaller shaft portion 194 having a gear member 196 on the outer end thereof.

In this case the drive adapter 186 is fully inserted into the housing extension 142 until the annular groove 190 comes into contact with the finger member 148. The right angle cartridge assembly 164 then is inserted over the drive adapter 186 and over the housing extension 142 until the inwardly extending annular ridge 168 comes into contact with the annular groove 158. Also it is noted that the gear member 196 of the drive adapter 186 will come into meshing engagement with the gear member 174 of the cartridge body 172.

Referring now to FIG. 11, reference character 198 generally indicates a drive housing assembly, having a cavity 200 therein for housing a motor 202 and associated wiring and switching generally indicated by reference character 204.

In this case the housing assembly 198 has a forwardly extending housing extension member 206 which has an annular groove around the outer periphery thereof and spaced from the forward end thereof. The drive motor 202 has a forwardly extending shaft member 210 which extends from the motor 202 through the housing extension 206 and terminates with a suitable gear member 212. In this case the right angle cartridge assembly 164 is simply inserted over the housing extension 206 until the inwardly extending annular ridge 168 comes into engagement with the annular groove 208 in order to secure the cartridge assembly 164 to the drive assembly 198. When the cartridge assembly 164 is fully installed on the drive assembly 198, the drive gear member 212 will be in meshing engagement with the gear member 174 of the rotatable cartridge body 172.

Figure 12:
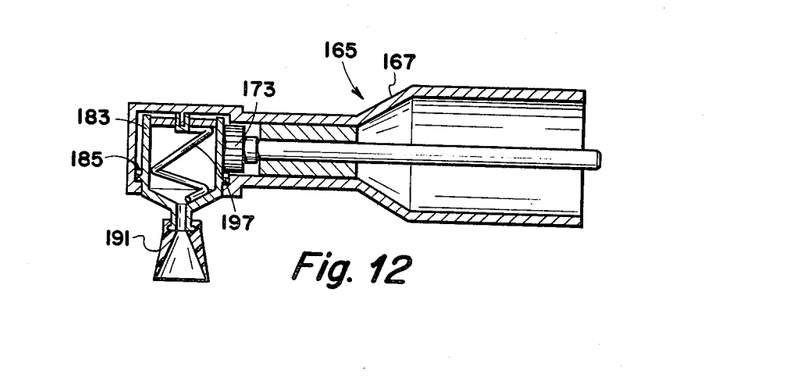
FIG. 12 is an elevational sectional view of a fourth modification of the apparatus of FIG. 2.
Figure 13:
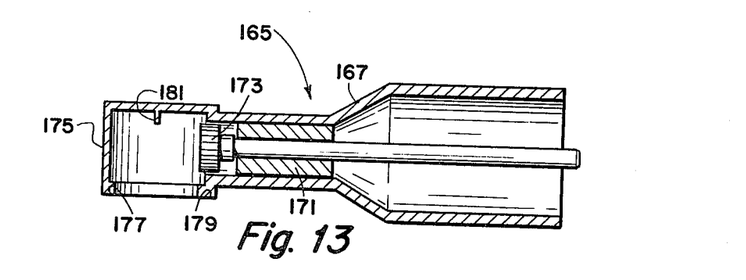
FIG. 13 is a detail, partially in section of the drive mechanism of the apparatus of FIG. 12.
Figure 14:
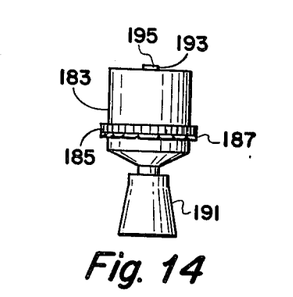
FIG. 14 is a detail elevational view of the polishing device of the apparatus of FIG. 12.

Referring to FIGS. 12, 13 and 14 of the drawings, reference character 165 generally indicates a single unit right angle housing adapter comprising a first portion 167 suitable for attaching to a dental doriot hand piece (not shown) and also for rotatably carrying an elongated drive shaft member 169. The drive shaft is carried by a suitable bushing member 171. The outer end of the drive shaft member 169 is provided with a gear member 173.

The outer end of the housing portion 167 is provided with a right angle cylindrical housing member 175 which is provided with an opening 177 in the bottom end thereof, the opening being provided with an inwardly extending lip member 179 around the inner periphery thereof. A wrenching element 181 is provided in the inside of the top of the housing and is downwardly extending as shown in FIGS. 12 and 13.

A disposable cartridge 183 is provided with a plurality of gear teeth 185 around the outer periphery thereof. An outwardly extending annular flange member 187 is provided around the outer periphery of the cartridge at the base of the gear teeth 185. The lower end of the cartridge 183 is provided with a cup member 91 and the upper end thereof is provided with a shaft member 193 having a wrenching element recess 195 therein. The shaft member 195 is again rigidly connected to a conveyor element 197 which is journalled inside the cartridge.

In use, the housing assembly 165 may be chucked onto a rotary dental hand piece or other drive mechanism. The cartridge 183 is then inserted upwardly into the housing member 175 until the flange member 187 around the cartridge is forced past the inwardly extending flange member 179 of the housing thereby locking the cartridge inside the housing member 175. This places the gear teeth 185 of the cartridge into meshing engagement with the gear teeth 173 of the housing assembly. Also the wrenching element recess 195 of the cartridge is placed into meshing engagement with the wrenching element 181 of the housing to prevent rotation of the conveyor mechanism inside the cartridge. Again, when power is applied to the drive shaft 169, rotation of the cartridge is effected, the interaction of which, with the conveyor element 197 causes paste to be forced to the interior of the cup 191.

Figure 15:
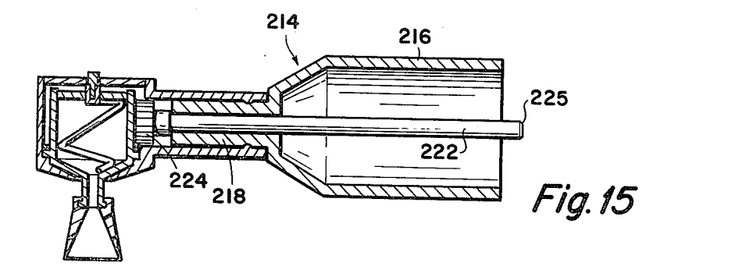
FIG. 15 is an elevational sectional view of a fifth modification of the apparatus in FIG. 2.
Figure 16:
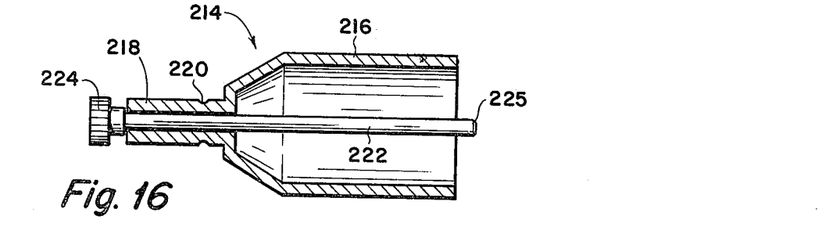
FIG. 16 is a detail sectional view of the drive housing of the apparatus of FIG. 15.
Figure 17:
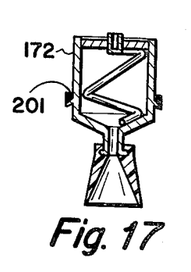
FIG. 17 is a detail sectional view of the polishing device of the apparatus of FIG. 15.

Referring to FIGS. 15, 16 and 17, reference character 214 generally indicates a drive housing having a housing body 216 and a forwardly extending housing extension 218 attached to the forward portion thereof. The extension 218 is provided with an annular groove 220 about the outer periphery thereof. An elongated drive shaft 222 is journalled within the housing extension 218, the outer end thereof being provided with a gear member 224 and the inner end thereof being terminated in a bevel or rounded end portion 225. The housing 216 and drive shaft 222 are adaptable to be fitted over the end of a dental rotary hand piece (not shown) whereby the end of the drive shaft 222 may be chucked onto the dental hand piece for rotation by an external drive means. In this case the right angle cartridge assembly 164 is fitted over the housing extension 218.

Figure 18:
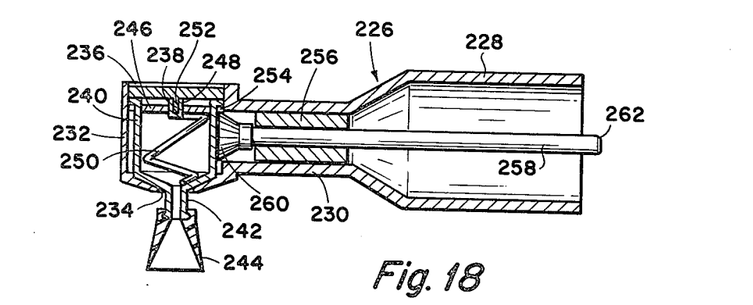
FIG. 18 is an elevational sectional view of a sixth modification of the apparatus of FIG. 2.

Referring now to FIG. 18, reference character 226 generally indicates a drive housing assembly comprising a body housing portion 228 which is insertable over a dentist's rotary drive hand piece, or doriot (not shown). The housing assembly 226 also comprises a forwardly extending housing extension barrel 230, the outer end thereof being provided with a cylindrical housing portion 232, the longitudinal axis of which is at a right angle to the longitudinal axis of the housing extension 230.

The bottom of the housing portion 232 is provided with an aperture 234 therein and the top of the housing portion 232 is provided with a removable cap member 236. A wrenching element protrusion 238 is centrally disposed on the inner surface of the cap member 236 and may be in the form of a common screwdriver tip. A disposable rotatable cartridge housing 240 is journalled within the housing portion 232 and is provided at the lower end thereof with a polishing cup attachment extension 242 which is insertable through the opening 234 in the housing portion 232. The polishing cup member 244 is then attachable to the extension 242.

The top of the disposable cartridge 240 is provided with a plate member 246 having a cylindrical opening for receiving a shaft member 248 of a conveyor member 250 which is journalled within the disposable cartridge 240. The shaft member 248 is provided with a wrenching element recess 252 for receiving the wrenching element 238 therein. An annular gear member 254 is provided around the outer periphery of the upper end of the cartridge 240.

The housing extension 230 is provided with a sleeve bearing member 256 for rotatably carrying an elongated drive shaft 258 therein. The outer end of the drive shaft 258 is provided with a gear member or serrated element 260 while the inner end thereof is rounded or beveled at 262 so that the shaft member is suitable for chucking into a dentist's doriot or hand piece (not shown).

In operation, the housing assembly 226 and associated drive shaft member 258 is either chucked into a dentist's doriot or may be provided with any suitable rotary drive source. The cap member 236 of the housing portion 232 may be removed so that a disposable cartridge pre-charged with paste material 240 may be inserted therein. When the device is fully inserted the gear member 254 will come into meshing engagement with the gear member 260 at the outer end of the drive shaft.

When the cap 236 is replaced onto the housing portion 232, the wrenching element 238 thereof is placed into meshing engagement with the wrenching element recess 252 to prevent rotation of the wiper conveyor member 250. Drive power is then applied to the shaft 258 for rotating the cartridge housing 240 in order to effect a polishing operation.

It is noted throughout this application that various arrangements of drive gears have been shown but which may be replaced with serrated discs or even friction pads shown at 201 in FIG. 17, and still fall within the scope of the invention.

From the foregoing it is apparent that the present invention provides a dental polishing apparatus whereby rotary polishing may be effected at the dentist's office or at home and whereby a supply of polishing compound or paste may be carried by disposable cartridges and continuously fed to the polishing cup in order to effect a professional type polishing job.

Whereas the present invention has been described in particular relation to the drawings attached hereto, other and further modifications apart from those shown or suggested herein may be made within the spirit and scope of the invention.

What is claimed is:
1. A tooth polishing device comprising:
(a) a hollow cylindrical cartridge for containing polishing paste therein;

(b) a hollow polishing cup secured to the first end of the cartridge and in open communication with the interior thereof;

(c) conveyor means carried inside the cartridge for urging the paste toward the first end of the cartridge when the cartridge is rotated; and (d) drive means operably connected to the cartridge and the conveyor means for rotating the cartridge and preventing rotation of the conveyor means.

2. A polishing device as set forth in claim 1 wherein the conveyor means is a helical wiper member.

3. A polishing device as set forth in claim 2 wherein the helical member is a helical ribbon flight.

4. A polishing device as set forth in claim 1 wherein the conveyor means is a helical wire member.

5. A polishing device as set forth in claim 1 wherein the drive means comprises a drive housing and a rotatable member carried thereby, means for rigidly securing the conveyor means to the housing to prevent rotation of the conveyor means, the cartridge being rotatably carried by the housing and operably connected to the rotatable means.

6. A polishing device as set forth in claim 5 wherein the drive means is a hand-held motor.

7. A polishing device as set forth in claim 5 wherein the drive means is a dentist's doriot hand piece.

8. A polishing device as set forth in claim 5 wherein the conveyor means also comprises a helical flight member, a shaft member, the inner end thereof being rigidly secured to the helical flight member, the outer end thereof being external of the second end of the cartridge and means carried by the drive housing for engaging the outer end of the shaft to prevent rotation thereof.

9. A polishing device as set forth in claim 8 wherein the means carried by the drive housing comprises a fastener tool while the outer end of the shaft comprises a mating fastener recess whereby upon mating the shaft to the housing, said fastener components prevent the rotation of the shaft with respect to the housing.

10. A polishing device as set forth in claim 8 wherein the means carried by the drive housing comprises a fastener recess while the outer end of the shaft comprises a mating fastener tool whereby upon mating the shaft to the housing, said fastener components prevent the rotation of the shaft with respect to the housing.

11. A polishing device as set forth in claim 5 wherein the rotational axis of the cartridge is disposed at a substantially right angle to the rotational axis of the rotatable member, and including drive transfer means.

12. A polishing device as set forth in claim 11 wherein the drive transfer means comprises cooperating gear members.

13. A polishing device as set forth in claim 11 wherein the drive transfer means comprises cooperating serrated members.

14. A cartridge for the polishing of teeth comprising:
(a) a rotatable cylindrical housing having a cavity therein for containing polishing paste material;
(b) a hollow polishing cup substantially rigidly secured to a first end of the housing for rotation therewith, the hollow portion thereof being in open communication with the housing cavity; and
(c) conveyor means journalled within the cavity, a shaft member having one end thereof rigidly secured to the conveyor means, the other end extending external of the cavity at the second end of the housing.

15. A cartridge as set forth in claim 14 including a removable plug for selectively closing said first end of the housing.

16. A cartridge as set forth in claim 14 wherein the conveyor means comprises a helical ribbon flight for urging the polishing paste towards said first end of the housing when the housing is rotated in one direction and the conveyor means is prevented from rotation.

17. A cartridge as set forth in claim 14 wherein the shaft member comprises a slidable plug member, a first end of which is attached to the conveyor means, a screw type conveyor flight attached to the opposite end of the plug member for cooperating with the inside wall of the housing to prevent paste material from moving out of the cavity around the end extending external of the cavity.

18. A cartridge as set forth in claim 14 wherein the external end of the shaft member is provided with a wrenching element to facilitate holding said shaft member and attached conveyor means against rotation with said housing.

* * * * *